United States Patent
Hee

(10) Patent No.: US 9,179,837 B2
(45) Date of Patent: Nov. 10, 2015

(54) CORNEAL STROMAL MAPPING

(71) Applicant: Optovue, Inc., Fremont, CA (US)

(72) Inventor: Michael Hee, Burlingame, CA (US)

(73) Assignee: Optovue, Inc., Fremont, CA (US)

( * ) Notice: Subject to any disclaimer, the term of this patent is extended or adjusted under 35 U.S.C. 154(b) by 38 days.

(21) Appl. No.: 13/836,258

(22) Filed: Mar. 15, 2013

(65) Prior Publication Data

US 2014/0049748 A1  Feb. 20, 2014

Related U.S. Application Data

(60) Provisional application No. 61/683,654, filed on Aug. 15, 2012.

(51) Int. Cl.
  *A61B 3/14* (2006.01)
  *A61B 3/00* (2006.01)
  *A61B 3/10* (2006.01)
  *A61B 3/107* (2006.01)

(52) U.S. Cl.
  CPC .............. *A61B 3/107* (2013.01); *A61B 3/102* (2013.01)

(58) Field of Classification Search
  CPC .......... A61B 3/103; A61B 3/14; A61B 3/113; A61B 3/1225; A61B 3/1015
  USPC .................. 351/206, 205, 200, 210, 221, 246
  See application file for complete search history.

(56) References Cited

U.S. PATENT DOCUMENTS

| | | |
|---|---|---|
| 5,293,871 A | 3/1994 | Reinstein et al. |
| 7,237,898 B1 | 7/2007 | Hohla et al. |
| 7,425,068 B2 | 9/2008 | Koest |
| 2007/0282313 A1 | 12/2007 | Huang et al. |
| 2008/0287929 A1 | 11/2008 | Holliday et al. |
| 2011/0032533 A1* | 2/2011 | Izatt et al. ............... 356/497 |
| 2013/0128222 A1* | 5/2013 | Huang et al. ............. 351/206 |

FOREIGN PATENT DOCUMENTS

WO  WO 2007/084694 A2  7/2007

OTHER PUBLICATIONS

Reinstein et al., "Arc-scanning Very High-frequency Digital Ultrasound for 3D Pachymetric Mapping of the Corneal Epithelium and Stroma in Laser in situ Keratomileusis," Journal of Refractive Surgery, vol. 16, Jul./Aug. 2000, 17 pages total.

Gatinel et al., "Contribution of the corneal epithelium to anterior corneal topography in patients having myopic photorefractive keratectomy," Journal of Cataract Refract Surgery 2007; vol. 33: pp. 1860-1865, 6 pages total.

Reinstein et al., "Corneal Epithelial Thickness Profile in the Diagnosis of Keratoconus," Journal of Refractive Surgery 2009; vol. 25: pp. 604-610, 7 pages total.

(Continued)

*Primary Examiner* — Dawayne A Pinkney
(74) *Attorney, Agent, or Firm* — Haynes and Boone, LLP

(57) ABSTRACT

A method of measurement is presented. A method of measurement according to some embodiments of the present invention includes obtaining a first measurement from a first imaging method; obtaining a second measurement from a second imaging method; combining the first and the second measurement to obtain a structural information and an image representation of a structure of an eye; calculating at least one shape parameter from the structural information; and displaying the image representation of the structure of the eye.

11 Claims, 9 Drawing Sheets

(56) References Cited

OTHER PUBLICATIONS

Mahmoud et al., "Simulation of Machine-Specific Topographic Indices for Use Across Platforms," Optometry and Vision Science, vol. 83, No. 9: pp. 682-693, Sep. 2006, 12 pages total.
International Search Report and the Written Opinion for related PCT International Application No. PCT/US2013/032315 mailed May 30, 2013, 8 pages.
Roberts et al., "The Advantage and Principle of Dual Scheimpflug Imaging for Analyzing the Anterior Segment of the Human Eye," Dept. of Opthalmology and Biomedical Eng Dept., Ohio State Univ. of Columbus Ohio and SIS Surgical Instrument Systems AG of Port Switzerland, Oct. 4, 2006, 8 pages.
Swartz et al., "Measuring the cornea: the latest developments in corneal topography," Lippincott Williams & Wilkins, 2007, pp. 325-333, 9 pages total.

* cited by examiner

CORNEAL STROMAL MAPPING

RELATED APPLICATIONS

This application claims priority to U.S. Provisional Application 61/683,654, filed on Aug. 15, 2012, which is herein incorporated by reference in its entirety.

BACKGROUND

1. Field of the Invention

Embodiments of the present invention relate generally to the field of optical coherence tomography and applications thereof. Specifically, embodiments of the present invention relate generally to methods and systems for measuring the geometric properties of the cornea.

2. Description of Related Art

The cornea and associated tear film are the primary refractive elements of the eye and the shape of the cornea is exceptionally important for vision. The shape of the cornea is commonly impacted in ectactic diseases, such as keratoconus, and in refractive and other surgical procedures.

Conventionally, the shape of the anterior surface of the cornea is measured using the principle of placido rings imaging. FIGS. 1A and 1B show an example of topographic imaging using the principle of placido rings imaging. As is commonly known in the arts, concentric rings 120 are projected onto the anterior corneal surface 110 of the eye 100, which is a convex and reflective surface. The variation in size of the virtual images of these reflected rings 120 can be used to derive the shape and refractive power of the anterior corneal surface, such as the axial map of the corneal curvature 150 derived using information from reflected ring positions as shown in FIG. 1B. Several corneal topography devices are commercially available using the placido rings imaging principle. In these devices, several topographic maps representing the derived anterior cornea surface are usually displayed, such as an axial/sagittal power or radius of curvature, tangential/instantaneous power or radius of curvature, and elevation relative to a reference surface. Although these topographic maps are commonly assumed to represent the shape of the anterior cornea surface, in actuality these topographic maps measure the shape of the corneal tear film, which is the first and primary reflective surface of the anterior surface of the eye. Therefore, topographic maps using the placido rings imaging principle can be disrupted in cases of poor or irregular tear film, especially those associated with dry eye conditions.

FIG. 2 is a diagram showing the anatomy of the cornea. The outer corneal epithelium 210 (or the anterior cornea), defining the outermost layer of the cornea 200, is a dynamic tissue which can remodel the cornea surface in the case of corneal ectactic disease or after refractive surgery. Changes in the thickness of the outer corneal epithelium 210 can mask changes in the underlying shape, such as the curvature of the corneal stroma 220 which is important in assessing corneal ectactic disease and corneal refractive surgical procedures. The inner corneal endothelium 230 defines the innermost layer of the cornea 200. In-between the outer corneal epithelium 210 and the corneal stroma 220 is the Bowman's membrane or the stromal-epithelial interface 215; while in-between the corneal stroma 220 and the inner corneal endothelium 230 is the Descemet's membrane 225. For example, epithelial thinning over an ectactic corneal stroma may prevent the detection of forme fruste keratoconus and other early ectactic disease important in the screening for refractive surgical procedures.

FIG. 3 is an exemplary schematic showing the effect of epithelial remodeling of the cornea. In the cornea 300 of FIG. 3, the corneal stroma 320 is deformed at deformation 350 due to some ectactic disease. However, the anterior corneal surface 340 is still relatively smooth and uniform due to the dynamic remodeling of the corneal epithelium 310. In these cases, measurement of the shape of the anterior corneal surface 340 alone, as performed by conventional placido topography, may not reveal the subtle changes in the shape of the corneal stroma, such as the damaged corneal stroma 320 in FIG. 3, as these changes may be masked by compensatory changes in the thickness of the corneal epithelium 310. On the other hand, an advantage of placido topography is its high sensitivity to small changes in corneal curvature as small changes in corneal height usually translates into larger measureable changes in the ring positions.

Epithelial remodeling may cause refractive regression after corneal laser refractive procedures. Also, refractive regression may be caused by changes in the shape of the cornea stroma which could indicate a structural weakness in the cornea. Measurements of the anterior corneal surface alone using conventional placido rings principles may not be able to distinguish these different causes of regression which are important in assessing corneal ectactic disease and corneal refractive surgical procedures.

One method of deriving additional information concerning the shape of the cornea stroma is to measure the shape of the posterior corneal surface, as the corneal endothelial thickness remains generally constant, contrary to the dynamic remodeling nature of the corneal epithelial layer as discussed above. Several commercially available clinical instruments attempted to measure the shape, such as curvature, of the posterior corneal surface. The Orbscan (Bausch & Lomb, Rochester, N.Y.) uses placido rings to measure the anterior corneal surface, and a scanning slit beam to determine conical thickness. Both measurements are used to derive the posterior corneal topography. The Pentacam (Oculus, Arlington, Wash.) employs the principle of Scheimpflug photography to measure both the anterior and posterior surfaces of the cornea. The Galilei (Zeimer, Alton, Ill.) uses a combination of placido rings imaging and Scheimpflug photography to generate topographic maps of both the anterior and posterior corneal surfaces. However, the spatial resolution of all these instruments is inadequate to accurately measure the shape and thickness of various tissue layers, such as the corneal epithelium, the corneal stroma, and the stromal-epithelial interface.

High-resolution cross-sectional imaging techniques, such as optical coherence tomography (OCT) and high-frequency ultrasound, have been used to measure the corneal epithelial thickness. Corneal epithelial thickness may be measured directly from OCT images using a computer algorithm available in commercial instrumentation, for example, in the RTVue (Optovue, Fremont, Calif.). Some methods were proposed to guide laser corneal surgery using OCT measurements of the corneal epithelial thickness. Some other methods disclose using either OCT, ultrasound, or Scheimpflug photography to map corneal epithelial thickness prior to laser epithelial ablation. Apparatus was also proposed to use high frequency ultrasound to measure corneal tissues thicknesses, including the epithelium and stroma. However, clinically useful measurement and data representation and display of the shape, such as curvature, of the corneal stromal/epithelial interface, using topographic maps of axial/sagittal power or radius of curvature, tangential/instantaneous power or radius of curvature, mean curvature, elevation, and elevation relative to a reference surface, in a manner similar to what a clinician is accustomed to in a routine clinical practice, are not available.

Therefore, methods and apparatus to obtain measurements of the corneal stroma, and in particular, to derive the shape of the anterior stromal/epithelial interface, and to display them using a topographic map in a similar manner to conventional mapping of the anterior corneal air/tear film interface are needed.

SUMMARY

A method of measurement is presented. A method of measurement according to some embodiments of the present invention includes obtaining a first measurement from a first imaging method; obtaining a second measurement from a second imaging method; combining the first and the second measurement to obtain a structural information and an image representation of a structure of an eye; calculating at least one shape parameter from the structural information; and displaying the image representation of the structure of the eye.

These and other embodiments are discussed further below with respect to the following figures.

DETAILED DESCRIPTION

Various embodiments of the present invention are described below with reference to the accompanying drawings. It is understood that figures have been simplified for the purposes of explanation herein and some elements that are conventional in the arts may be omitted.

Corneal topography is an important clinical tool for measuring the shape of the anterior corneal surface, and is useful in the diagnosis of corneal ectatic disease and in the pre- and post-operative evaluation of corneal refractive surgery. Changes in the shape of the corneal stroma may be masked by remodeling of the corneal epithelium and may not be visible using conventional clinical corneal topography methods.

In accordance with some embodiments, a method for measuring the shape of the anterior corneal stromal interface, displaying the shape in the form of a topographic map or three-dimensional representation, and computing parameters such as axial or sagittal power or radius of curvature, tangential or instantaneous power or radius of curvature, mean curvature, elevation, elevation relative to a reference surface, and screening parameters for ectatic disease, such as KISA % index, surface asymmetry index, and others are disclosed.

Figure 9:
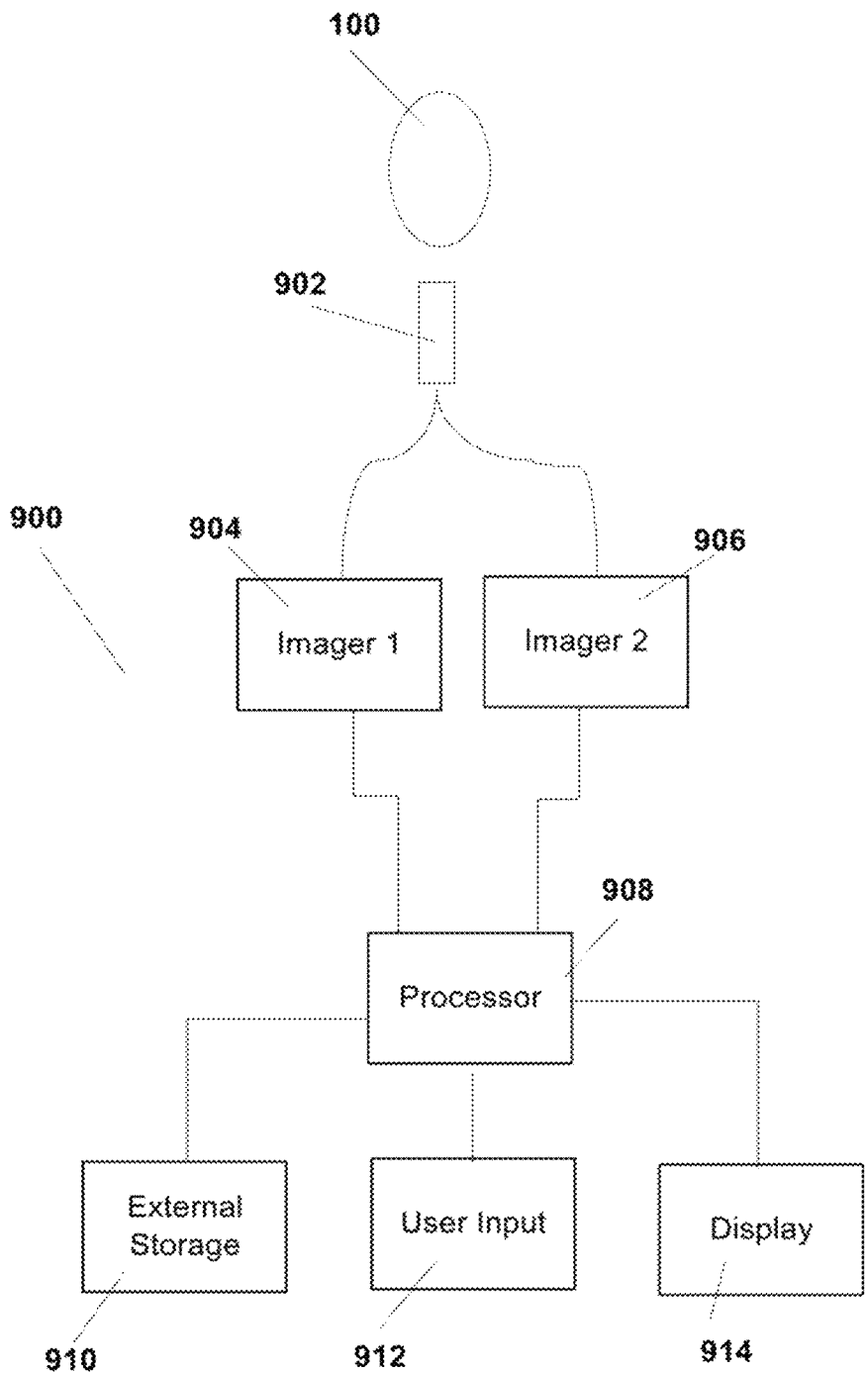
FIG. 9 illustrates an image processing system according to some embodiments of the present invention.

FIG. 9 illustrates an image processor 900 according to some embodiments of the present invention. As shown in FIG. 9, two imagers 904 and 906 are coupled with coupler 902 to obtain images of eye 100. Imagers 904 and 906 can include, for example, placebo imagers, ultrasonic imagers, Scheimpflug photo imagers, or OCT imagers. In most embodiments, imagers 904 and 906 are two imagers that utilize different imaging techniques. Imager 904 and imager 906 are coupled to a processor 908. Processor 908 can be any processor, for example a computer system with one or more processors and internal memory. Processor 908 can manipulate and store images received by imagers 904 and 906 and can control the operation of imagers 904 and 906. In some embodiments, processor 908 can further be coupled to a display 914, user input devices 912, and external data storage 910.

Figure 4:
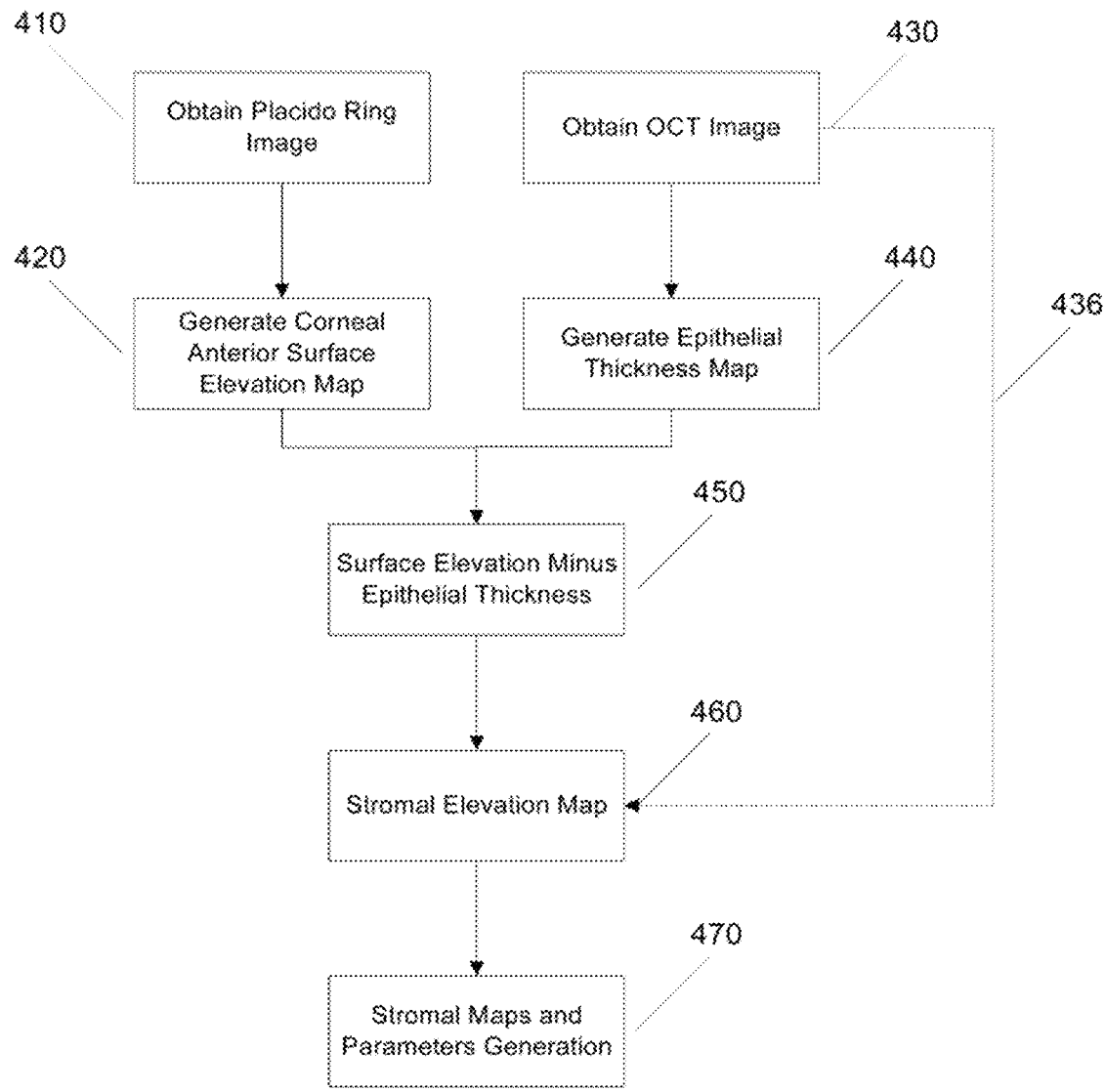
FIG. 4 shows a block diagram illustrating a method according to some embodiments of the present invention.

In some embodiments, imager 904 can be placebo ring imager and imager 906 can be an OCT imager. FIG. 4 shows a block diagram illustrating a method of obtaining the corneal stromal mapping according to some embodiments of the present invention. The method can be executed on processor 908 and the results displayed on display 914. According to FIG. 4, the first step is to create a placido ring image 410 using the placido ring imaging principle. Then, the next step 420 is to generate one or more corneal anterior surface elevation maps. At the same time, or substantially close in time, one or more OCT images are obtained in step 430. Then, the epithelial thickness map is generated in step 440 using the OCT image(s) from step 430. In the next step 450, the epithelial thickness information can then be subtracted from the surface elevation information from step 420. Then, the stromal elevation map can be generated in step 460. In addition, one or more stromal maps and stromal parameters can then be calculated for further analysis and evaluation, as described in step 470. Alternatively, according to FIG. 4, the stromal elevation map in step 460 can be generated directly from using OCT image(s) in step 430 alone through a direct generation method 436. Details of the embodiments in FIG. 4 are further described in the following descriptions.

Alternative Direct Method

In some embodiments, the shape, such as the curvature, of the interface between the corneal epithelium 210 and corneal stroma 220 can be determined directly from features detected by a cross-sectional imaging technique such as optical coherence tomography (OCT), high-resolution ultrasound, or Sheimpflug photography. This step is illustrated by path 436, which takes the OCT image generated in step 430 directly to evaluation step 460. A normal corneal epithelium 210 has a thickness of approximately 50 to 70 microns. Therefore, a high-resolution imaging technique can be used to accurately delineate the boundary between the epithelium 210 and the stroma 220, defined by the Bowman's membrane/stromal-epithelial interface 215. OCT is ideally suited for this purpose because it provides higher resolution than ultrasound can provide due to the use of a smaller optical wavelength. A commercially available Fourier domain OCT system with a longitudinal resolution of 5 microns can distinguish reflections from the anterior and posterior surface of Bowman's membrane 215 accurately. The location of this interface/Bowman's membrane 215 can then be determined using various image processing algorithms on the acquired cross-sectional images.

Figure 5:
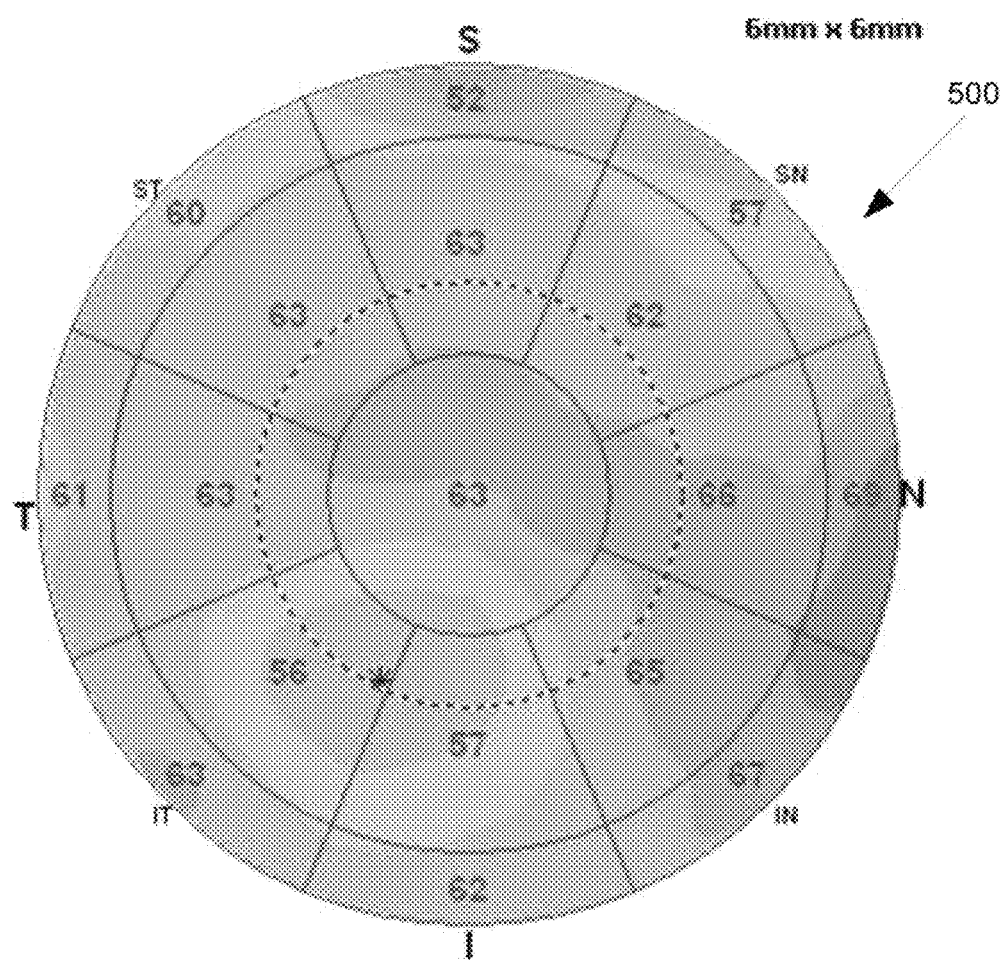
FIG. 5 illustrates an exemplary topographic map of corneal epithelial thickness obtained using optical coherence tomography according to some embodiments.
Figure 6:
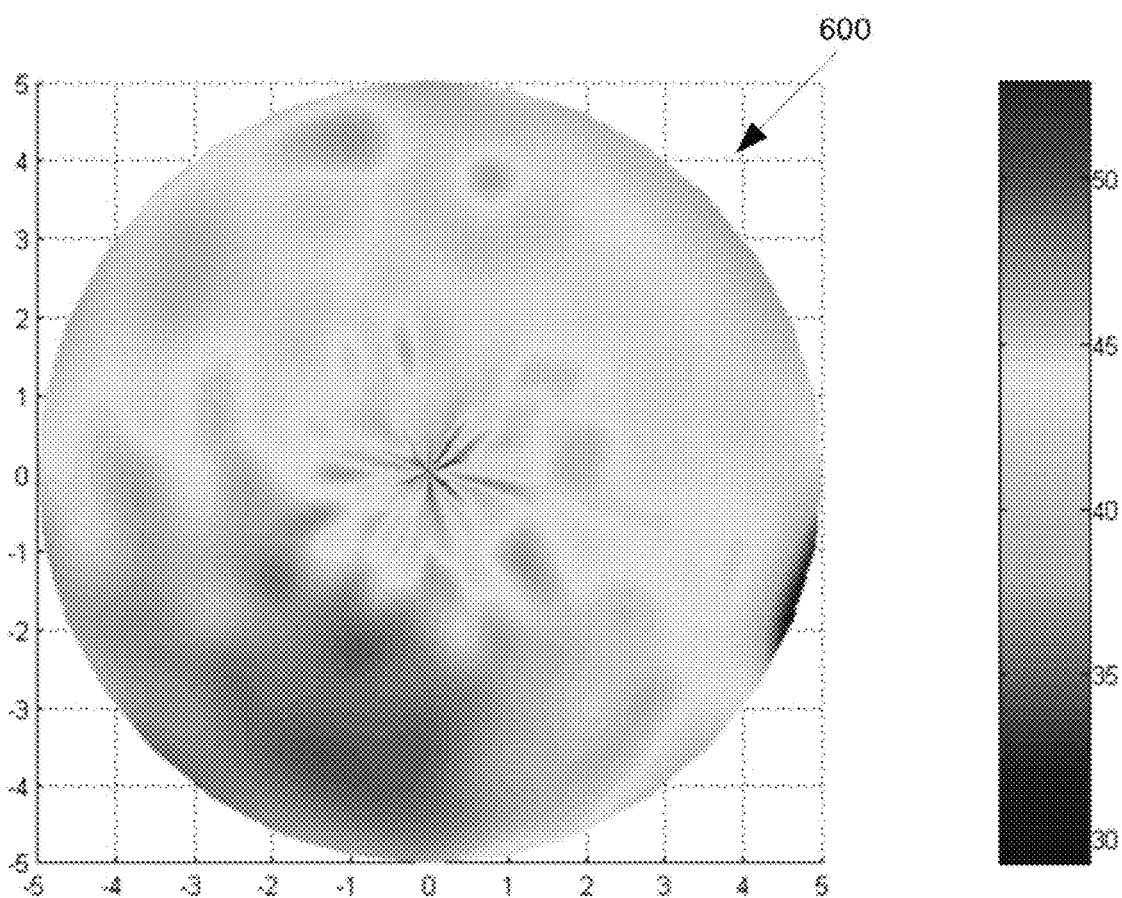
FIG. 6 illustrates an exemplary topographic map of the anterior corneal stromal interface obtained directly from optical coherence tomography measurements in some embodiments.

FIG. 5 illustrates an exemplary topographic map 500 of corneal epithelial thickness map using the OCT imaging method directly as in path 436. The topographic map 500 is constructed directly from multiple OCT images alone using commonly known image processing techniques, such as image segmentation and data interpolation. FIG. 6 is an exemplary topographic map 600 of the stromal corneal curvature of step 470 obtained directly by measuring the epithelial-stromal interface 215 from OCT images in step 430.

In some embodiments of the present invention, the shape, such as the radius of curvature, of the corneal stromal-epithelial interface 215 can be displayed as a three-dimensional or topographic map in a manner intuitive for clinicians adept at interpreting standard placido based topography of the anterior corneal surface. These topographic maps in step 460 can provide parameters such as axial/sagittal power or radius of curvature, tangential/instantaneous power or radius of curvature, mean curvature, elevation, and elevation relative to a reference surface such as the best fit sphere or the best fit toric ellipsoid important for assessing corneal ectatic disease and corneal refractive surgical procedures, as indicated in step 470 in FIG. 4.

It is well-known in the arts that voluntary and involuntary patient motion during image acquisition will likely give rise to motion artifacts. The same patient motion might give rise to motion artifacts when directly measuring the reflection from the Bowman's membrane 215 using OCT alone as in step 436, particularly in the axial direction.

Figure 7:
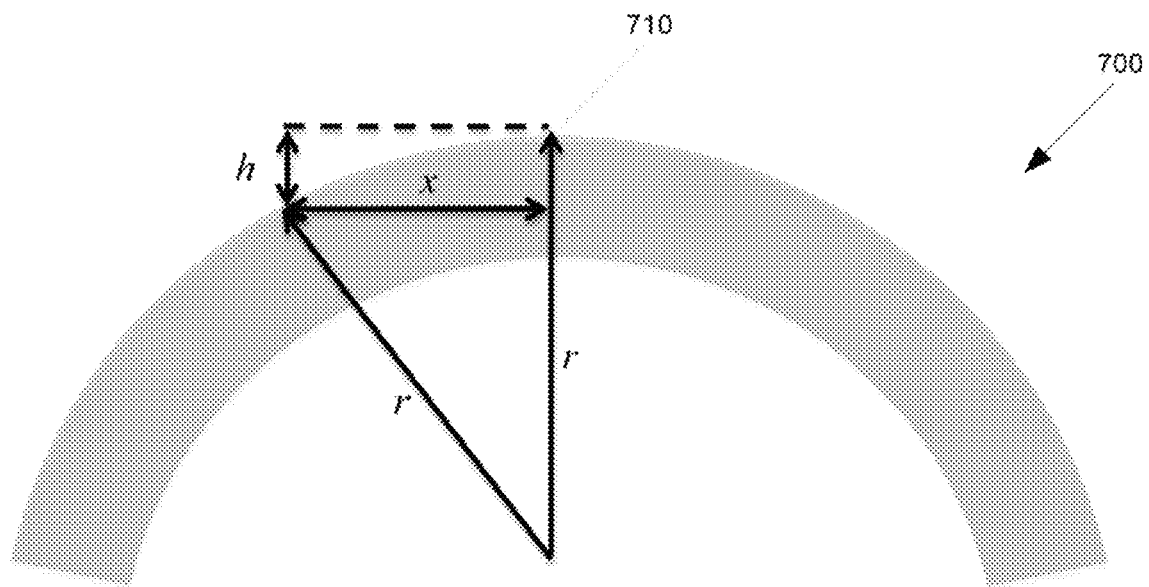
FIG. 7 is a diagram showing the relationship between the radius of curvature of the cornea to the elevation and radial distance from the axis of the corneal apex.

The sensitivity of curvature measurements of a corneal interface to axial motion may be determined by equations linking a measured corneal power F or radius of curvature r to the corneal elevation. In ophthalmic practice, radius of curvature r is typically converted to units of power expressed in diopters (D), where the power F is given by $F=(n-1)/r$, where n is the keratometric index and is typically taken to be 1.3375. The average radius of curvature of the cornea is approximately r=7.6 mm yielding an average corneal power F=44.4 D. A commercially available placido based topography system is able to measure the corneal radius of curvature to within approximately ±0.25 D so that the radius of curvature can be determined to be within approximately $\Delta r = \Delta F \cdot (n-1)/F^2 = 43$ microns. If the cornea is assumed to have an approximately constant radius of curvature, the corneal height h of the corneal surface varies by approximately $h \approx x^2/(2r)$ from the corneal apex to a peripheral location on the cornea, where x denotes the radial distance from the corneal apex to the peripheral location. FIG. 7 shows the relationship between the radius of curvature r, the corneal height h, and the radial distance x from the corneal apex 710 of the cornea 700. In order to determine the corneal radius of curvature r to be within 43 um, i.e. $\Delta r$=43 um, the corneal height h can be measured to be within $\Delta h = -\Delta r \cdot x^2/(2r^2)$. For clinically acceptable power accuracy of 0.25 D, at an x=1 mm distance from the center/apex 710 of the cornea 700 with a radius of curvature r=7.6 mm, the height h is required to be within 0.37 microns; at x=3 mm, the height would be required to be within 3.3 um; and at a distance x=0.5 mm from the center 710, the height accuracy would be less than approximately 0.1 micron. Therefore, accurate absolute measurements of curvature of any corneal interface layer can easily be impacted by patient or eye motion of less than 1 micron, especially in the axial direction.

Figure 8:
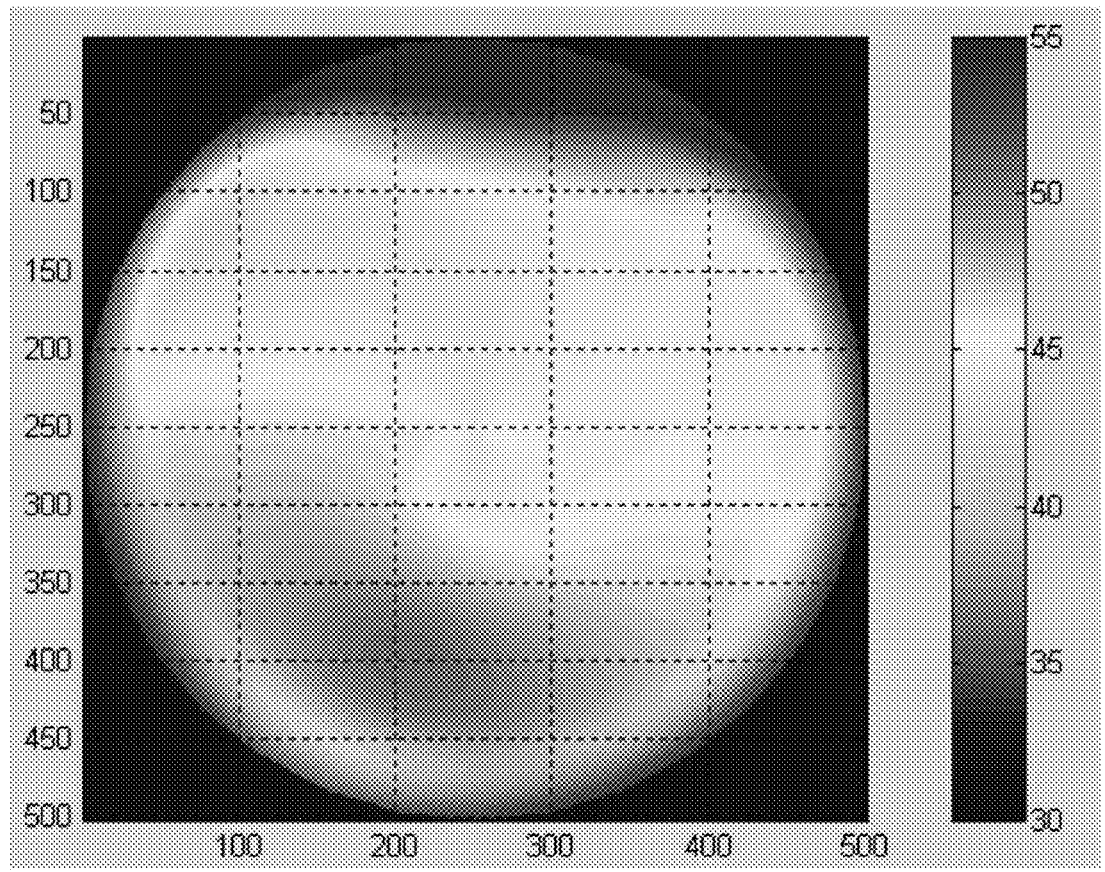
FIG. 8 illustrates an exemplary topographic map of a stromal corneal curvature in some embodiments.

Due to the impact of patient and eye movement on the accuracy of measurement, commercially available OCT instruments report only the corneal epithelial thickness as in FIG. 5 rather than corneal stromal curvature or shape (as shown in FIG. 8 below). A measurement of epithelial thickness is relatively insensitive to patient or eye motion in the axial direction since such motions will move both the anterior and posterior epithelial boundaries simultaneously. Alternatively, single measurements may be obtained rapidly with limited impact from patient and eye motion and a relatively accurate map of the epithelial thickness can then be constructed from a sequence of single thickness measurements obtained at different locations.

Method Using Multiple Imaging Modalities

According to some embodiments, in order to reduce the impact of patient and eye motion described above, the shape or the curvature of the corneal epithelial-stromal interface 215 can be determined using information from one or more imaging modalities. As described in FIG. 4, placido image(s) can be performed in step 410 to obtain the shape of the corneal anterior surface in step 420. At the same time, OCT image(s) can be performed in step 430 to obtain the epithelial thickness map in step 440. In step 450, the epithelial thickness map can be subtracted from the corneal anterior surface map to generate stromal elevation map(s) in step 460. Then, clinically useful information and information accustomed to medical professional, such as the shape of the corneal epithelial-stromal interface 215 can be determined as in step 470.

Determining the position of the epithelial-stromal interface 215 in this manner described in FIG. 4 can be less sensitive to axial motion artifacts. The placido image used to define the shape of the anterior corneal 210 is obtained rapidly by an almost instantaneous snapshot of the reflection of the placido rings from the air/tear film interface; therefore, the measurement is less affected by small axial motion. Also, axial motion has minimal impact on the epithelial thickness measurement obtained using OCT method, as described above, because both the anterior and posterior epithelial boundaries move simultaneously in response to axial movement. Therefore, combining placido anterior elevation from step 420 with OCT measurement of epithelial thickness from step 440 as in step 450 to yield a measurement of the corneal stromal-epithelial interface 215 and other clinically useful information, such as image map and parameters, can be much less sensitive to motion artifact than direct measurement, such as indicated in path 436 in FIG. 4 of using OCT measurement alone. Using information from multiple modalities is advantageous.

As described in FIG. 4, using OCT as a modality to obtain measurement, such as the epithelial thickness measurement, advantageous to both ultrasound and Scheimpflug photography. Unlike either OCT or placido imaging, ultrasound imaging requires contact between an imaging probe or fluid coupling for the eye. Therefore, ultrasound imaging cannot be performed simultaneously with placido imaging. Scheimpflug and placido imaging may be performed simultaneously; however, unlike OCT, Scheimpflug imaging lacks the high longitudinal resolution necessary to accurately and consistently identify the boundary between the corneal stroma 220 and epithelium 210. FIG. 8 shows an exemplary topographic map of the stromal corneal curvature obtained by measuring the anterior corneal surface using the placido rings imaging principles and the epithelial thickness measurement by optical coherence tomography according to some embodiments of the present invention.

Several parameters based on the shape of the anterior corneal 210 (outer corneal epithelium) have been developed to enhance the utility of placido topography to screen for corneal ectatic disease such as keratoconus. These parameters typically incorporate local or geographic measurements of the radius of curvature or power of the anterior corneal surface 210. As the parameters were originally developed for use with placido imaging, they are typically calculated from measurements based on predefined ring numbers. Therefore, depending on the size and number of projected rings, the details of performing the calculations may differ between placido based instruments. In some embodiments, the calculations can be made independent of placido ring size by defining the parameters in terms of geographic location on the cornea, rather than ring number, when generating information as described in step 470.

Key corneal shape parameters that are commonly used, all of which depend on dioptric power measurements of the shape of the anterior cornea 210 at varying geographic locations, include the following:

K (keratometry value)—average dioptric power in the center of the cornea.

I-S (inferior-superior difference)—difference between inferior and superior average dioptric values in an annulus with approximately 3 mm radius.

Sim K1 and Sim K2 (simulated keratometry values)—steepest dioptric power and power 90° away in the perpendicular meridian, typically evaluated in an annulus of 3 mm diameter.

SDP (standard deviation power)—the standard deviation of all the dioptric powers present on the corneal map.

DSI (differential sector index)—the greatest difference in average power between any two 45° sectors, typically corrected by sector area.

OSI (opposite sector index)—the greatest difference in average power between any opposite 45° sectors, typically corrected by sector area.

CSI (center/surround index)—difference in the average area-corrected power in the central 3 mm versus the average area-corrected power in the surrounding annulus from 3 to 6 mm.

SAI (surface asymmetry index)—weighted average of the difference in dioptric power between points 180° apart.

SRI (surface regularity index)—running sum of any difference in dioptric power gradient between successive ring pairs.

IAI (irregular astigmatism index)—area corrected version of SRI.

KPI (keratoconus prediction index)—a composite index reflecting the percentage probability of keratoconus based in the parameters DSI, OSI, CSI, SAI, sim K, IAI, and area of the cornea analyzed.

SRAX (skewed radial axis of astigmatism)—180° minus the difference between the angle of the steepest axis above the horizontal meridian and the steepest axis below the horizontal meridian.

KISA %—a composite index based on K, I-S, sim Ks, and SRAX, used to predict keratoconus.

Figure 1:
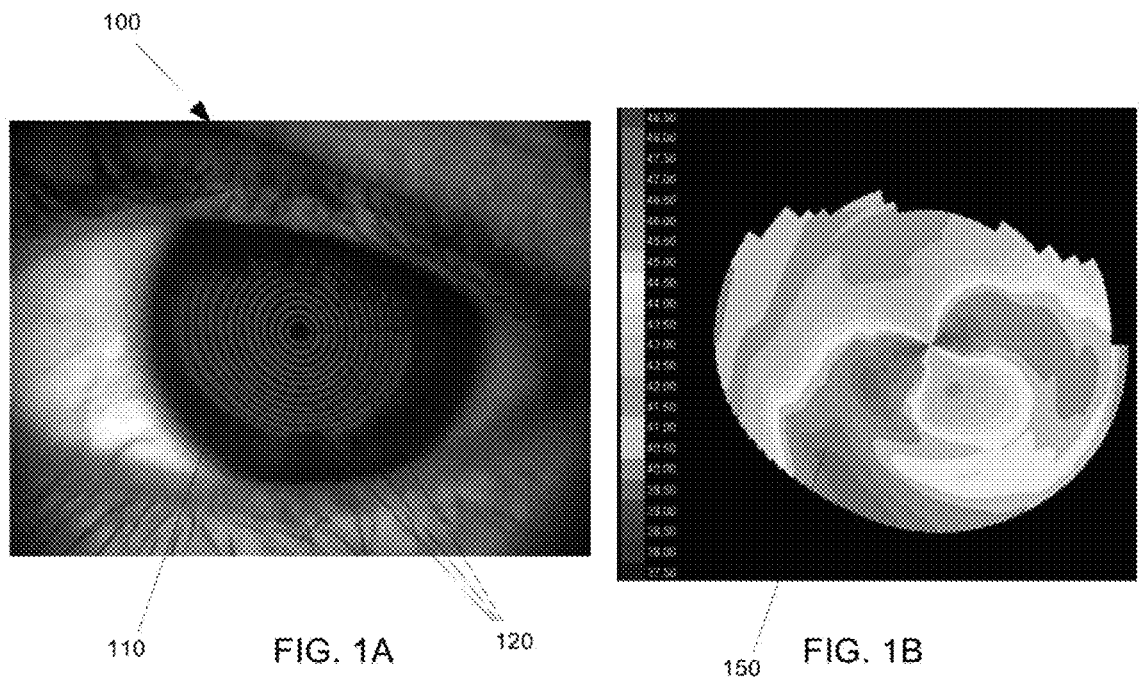
FIGS. 1A and 1B show an exemplary topographic image created using the placido rings imaging principle.
Figure 2:
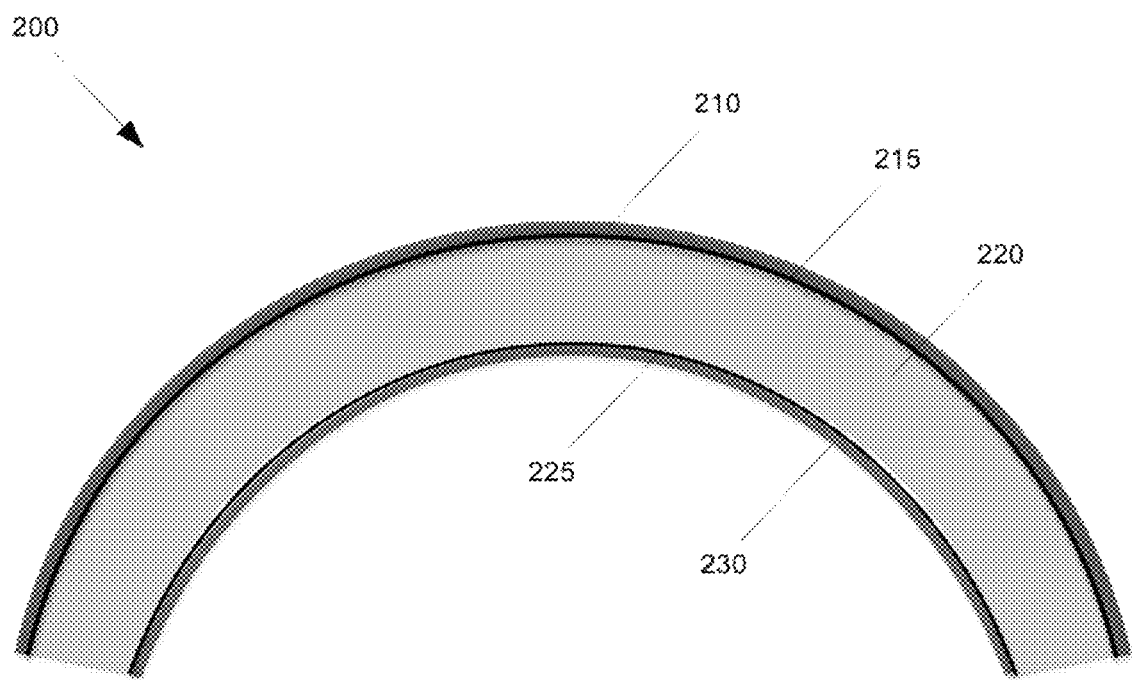
FIG. 2 is a diagram showing the anatomy of the cornea.
Figure 3:
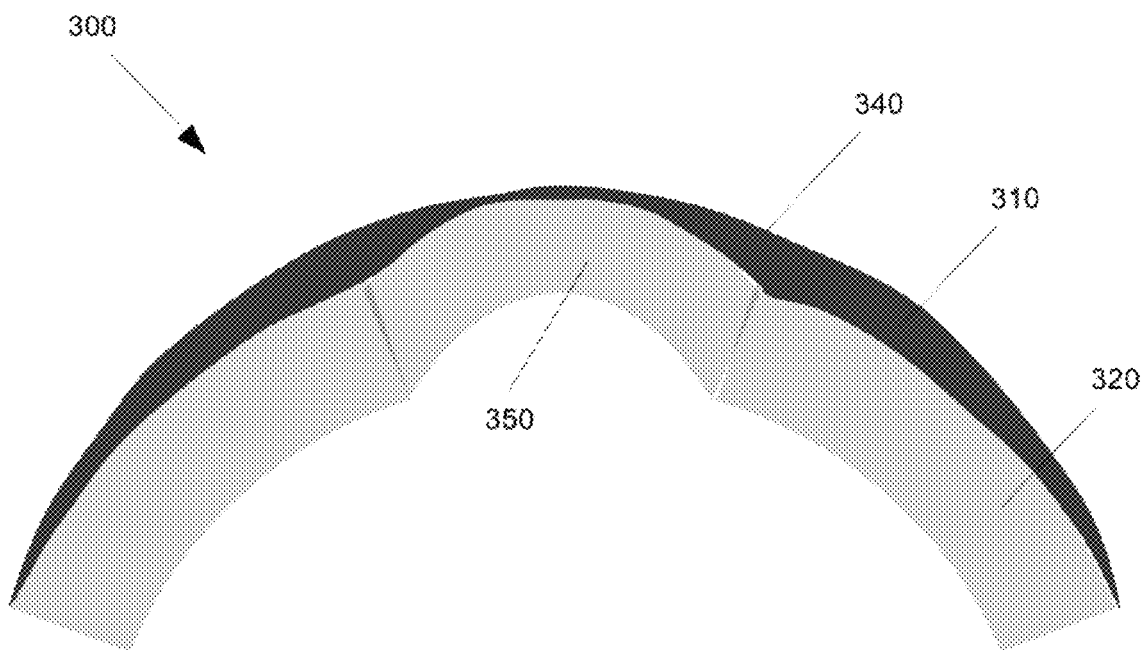
FIG. 3 is an exemplary schematic showing the effect of epithelial remodeling of the cornea.

However, the predictive power of the above ectasia screening parameters depending on measurement of the shape of anterior cornea may be impacted by the dynamic compensatory remodeling in the thickness of the corneal epithelium 210 that usually mask the changes in shape of the corneal stroma 220, as described above with FIG. 3. Therefore the predictive power of any particular parameter or composite index discussed above can likely be enhanced if measurements of the shape of the corneal stromal-epithelial interface 215 are substituted for the traditional measurements of the corneal epithelial/anterior surface shape, according to some embodiments of the present invention. It should be apparent to those skilled in the art that any corneal shape parameter that relies on measurements derived from the shape of the anterior-epithelial surface can likely be improved by substituting measurements derived from the shape of the stromal-epithelial interface 215, obtained using the method described in FIG. 4.

It should be understood that certain embodiments or portions thereof may be implemented in hardware, firmware, or software. If implemented in software, the software may be any language that can cause a processor to be configured in a manner to perform embodiments discussed herein or equivalents thereof. The software may be in the form of executable instructions and stored on any non-transient or transient, computer-readable medium that can be loaded and executed by a general purpose or application-specific processor.

While the methods and devices described herein have been particularly shown and described with references to example embodiments thereof, it will be understood by those skilled in the art that various changes in form and details may be made therein.

The invention claimed is:

1. A method of measurement, comprising:
   obtaining a corneal anterior surface map from a first imaging method;
   obtaining an epithelial thickness map from a second imaging method;
   combining the corneal anterior surface map and the epithelial thickness map to obtain a stromal elevation map and a topographic map of a stromal corneal curvature; and
   displaying the topographic map, wherein the combining the corneal anterior surface map and the epithelial thickness map includes calculating the difference between the corneal anterior surface map and the epithelial thickness map.

2. The method of claim 1, further comprising determining a corneal epithelial surface, a corneal stroma, or an anterior corneal stromal interface of an eye.

3. The method of claim 1, wherein the first imaging method can be a placido imaging, an ultrasound imaging, a scheimpflug photography, or an optical coherence tomography.

4. The method of claim 1, wherein the second imaging method can be an ultrasound imaging, a scheimpflug photography, or an optical coherence tomography.

5. The method of claim 1, further comprising calculating at least one shape parameter from the corneal anterior surface map and the epithelial thickness map, wherein the at least one shape parameter can be an axial power (sagital power), axial curvature (sagittal curvature), tangential power (instantaneous power), tangential curvature (instantaneous curvature), mean curvature, elevation, and elevation relative to a reference surface.

6. The method of claim 1, further comprising calculating at least one corneal ectasia screening parameter based on structural information of a corneal epithelial surface.

7. The method of claim 1, further comprising calculating at least one corneal ectasia screening parameter based on structural information of a corneal epithelial-stromal interface.

8. A method of measurement, comprising:
   obtaining at least a corneal anterior surface map from a first imaging method selected from a group consisting of a placido image, an ultrasound, a Scheimpflug photography, and an optical coherence tomography (OCT);
   obtaining at least an epithelial thickness map from a second imaging method selected from a group consisting of an OCT, a high-resolution ultrasound, or a Sheimpflug photography;
   processing the corneal anterior surface map and the epithelial thickness map to obtain an interface between a corneal epithelium and a corneal stroma;
   determining at least one shape parameter of the interface;

calculating at least one corneal ectasia screening parameter;

generating a topographic or three-dimensional representation of the interface; and displaying the topographic or three-dimensional representation, wherein the processing of the corneal anterior surface map and the epithelial thickness map includes calculating the difference between the corneal anterior surface map and the epithelial thickness map.

9. An image processing system, comprising:

a first imager;

a second imager; and a processor coupled to the first imager and the second imager, the processor executing instructions to:

obtain a corneal anterior surface map from the first imager;

obtain an epithelial thickness map from the second imager;

combine the corneal anterior surface map and the epithelial thickness map to obtain a stromal elevation map and a topographic map of a stromal corneal curvature; and display the topographic map, wherein the combining the corneal anterior surface map and the epithelial thickness map includes calculating the difference between the corneal anterior surface map and the epithelial thickness map.

10. The imager of claim 9, wherein the first imager can be a placido imager, an ultrasound imager, a scheimpflug photography imager, or an optical coherence tomography imager.

11. The imager of claim 9, wherein the second imager can be an ultrasound imager, a scheimpflug photography imager, or an optical coherence tomography imager.

* * * * *